(12) United States Patent
Bröckl et al.

(10) Patent No.: US 9,060,882 B2
(45) Date of Patent: Jun. 23, 2015

(54) JOINT MECHANISM

(75) Inventors: Heinz Bröckl, Vienna (AT); Hans Dietl, Gablitz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 68 days.

(21) Appl. No.: 13/876,565

(22) PCT Filed: Sep. 23, 2011

(86) PCT No.: PCT/EP2011/004772
§ 371 (c)(1),
(2), (4) Date: Mar. 28, 2013

(87) PCT Pub. No.: WO2012/041463
PCT Pub. Date: Apr. 5, 2012

(65) Prior Publication Data
US 2013/0190896 A1  Jul. 25, 2013

(30) Foreign Application Priority Data

Sep. 28, 2010  (DE) .......................... 10 2010 046 690

(51) Int. Cl.
*A61F 2/64*  (2006.01)
*A61F 2/70*  (2006.01)
(Continued)

(52) U.S. Cl.
CPC .............. *A61F 2/64* (2013.01); *A61F 2002/707* (2013.01); *A61F 2/646* (2013.01);
(Continued)

(58) Field of Classification Search
CPC ........... A61F 2/604; A61F 2/608; A61F 2/64; A61F 2002/608; A61F 2002/6854; A61F 2005/0158; A61F 2220/0033; E05D 11/1007; E05D 11/1014; F16B 5/0044; F16B 5/0084

USPC ....................... 623/26–30, 38–48, 53, 60–65; 292/194–195, 198, 340; 403/83, 91, 93
See application file for complete search history.

(56) References Cited

U.S. PATENT DOCUMENTS 302,433 A * 7/1884 Scott ............................... 623/43
3,533,651 A * 10/1970 Prahl .............................. 403/93
(Continued)

FOREIGN PATENT DOCUMENTS

DE     3414869 A1    10/1985
DE    19810385 A1     9/1999
(Continued)

OTHER PUBLICATIONS

Stanfield, Morgan. Adaptive Summer Fun. The O&P Edge. Jun. 2009.*

(Continued)

*Primary Examiner* — Thomas J Sweet
*Assistant Examiner* — Christie Bahena
(74) *Attorney, Agent, or Firm* — Holland & Hart

(57) ABSTRACT

The invention relates to a join mechanism of a knee orthosis or knee prosthesis, having a first part (14), a second part (15), which is pivotable relative to the latter, and attachment means (2) for securing the joint mechanism (1) to a user of the knee orthosis or knee prosthesis, and having a locking mechanism (4, 40) with which a pivoting of the two parts (14, 15) relative to each other in a flexion direction is prevented by a form-fit element (4) which is arranged movably on the second part (15) and which, in the locking state, engages with a form fit in a recess (40) assigned to the first part (14), wherein the form-fit element (4) is mounted rotatably on the second part (15) and has a contour which, in the locked position, protrudes into the recess (40) and, in the released position, allows the first part (14) to pivot past the bearing of the form-fit element (4).

17 Claims, 6 Drawing Sheets

(51) Int. Cl.
*A61F 2/50* (2006.01)
*A61F 2/68* (2006.01)
*A61F 2/74* (2006.01)
*A61F 5/01* (2006.01)

(52) U.S. Cl.
CPC *A61F 2002/5006* (2013.01); *A61F 2002/5072* (2013.01); *A61F 2002/6854* (2013.01); *A61F 2002/745* (2013.01); *A61F 2002/748* (2013.01); *A61F 2005/0158* (2013.01); *A61F 2220/0033* (2013.01)

(56) References Cited

U.S. PATENT DOCUMENTS

| | | | | |
|---|---|---|---|---|
| 3,833,942 | A | * | 9/1974 | Collins .......................... 623/60 |
| 4,520,804 | A | * | 6/1985 | DiGeorge ...................... 602/16 |
| 6,139,586 | A | | 10/2000 | Wagner et al. |
| 2004/0225242 | A1 | | 11/2004 | Lidolt et al. |
| 2005/0149203 | A1 | | 7/2005 | Andrysek et al. |
| 2006/0167562 | A1 | * | 7/2006 | Williams et al. ................ 623/24 |
| 2007/0010772 | A1 | * | 1/2007 | Ryan ............................... 602/26 |
| 2007/0083272 | A1 | | 4/2007 | Van De Veen et al. |
| 2011/0009981 | A1 | * | 1/2011 | Okuda et al. .................... 623/32 |

FOREIGN PATENT DOCUMENTS

| | | |
|---|---|---|
| DE | 10311189 A1 | 10/2004 |
| DE | 10351916 A1 | 6/2005 |
| DE | 202006007461 U1 | 10/2007 |
| EP | 0016268 A1 | 10/1980 |
| GB | 691264 | 5/1953 |
| RU | 2026655 C1 | 1/1995 |
| RU | 2096026 C1 | 11/1997 |
| RU | 74291 U1 | 6/2008 |
| WO | 2009110097 A1 | 9/2009 |

OTHER PUBLICATIONS

PCT International Search Report for PCT International Patent Application No. PCT/EP2011/004772, mailed Dec. 19, 2011.

* cited by examiner

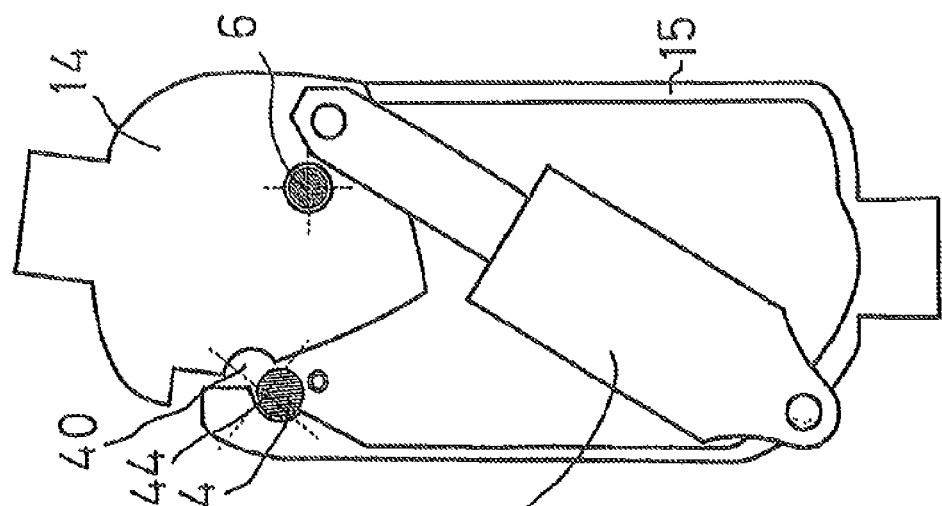
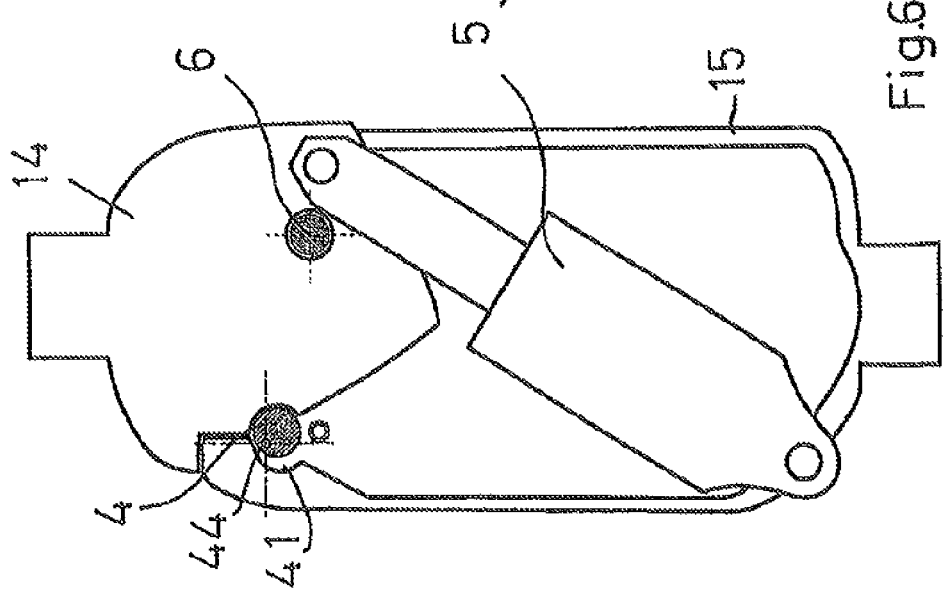

JOINT MECHANISM

BACKGROUND

The invention relates to a joint mechanism of a knee orthosis or a knee prosthesis having a having a first part and a second part, which is pivotable in relation thereto, and connection means for fastening the joint mechanism on a user of the knee orthosis or knee prosthesis having a locking mechanism, by way of which a pivoting of the two parts relative to one another in the direction of flexion is prevented by means of a positive locking element which is arranged so as to be displaceable on the second part and in the locking state engages in a positive locking manner in a recess associated with the first part.

Knee joints, either for ortheses or prostheses, which are lockable in a specific position, are designated as locking knee joints. There are different embodiments of locking knee joints which predominantly serve the purpose of giving the user of the knee joint as much security as possible. Prosthesis wearers are, in particular, a patient group in which inactive, for the most part geriatric patients are more likely to be present, to whom, when walking and standing, an increased feeling of security is conveyed by a knee joint locked in the extended position. Said group of prosthesis users is not in a position to prevent a sudden, unwanted bending of the joint by means of compensating movements. Locking in the extended position can also be sensible for orthosis users when the musculature system present is not sufficient to hold the leg stable in certain situations.

DE 103 51 916 A1 shows a prosthesis knee joint having an upper part and a lower part fastened thereto by means of a multi-axial joint mechanism. The lower part is always pivotable in an unrestricted manner in the direction of extension, a locking element is provided which holds a secondary valve of a hydraulic damper unit in the open position.

DE 20 2006 007 461 U1 describes a prosthesis knee joint having an upper part and a lower part fastened thereto in an articulated manner. A lockable and unlockable blocking mechanism, which, when locked, prevents a pivoting of the upper part in relation to the lower part, is provided between the upper part and the lower part.

DE 103 11 189 A1 describes an orthopedic aid having parts which are movable in relation to one another and a locking mechanism for locking the two parts in a predetermined relative position and for unlocking the parts to release the movement of the parts with respect to one another. The orthopedic aid is realized, in particular, as an orthosis. An end portion of a joint lower part is provided with a radial recess into which a locking pin, which is mounted on the joint upper part, engages by way of a lower end which is formed so as to complement the recess. At its upper end, the locking pin merges into a cylindrical core which is axially movable in an interior of an electric coil. When current is directed through the coil, the locking pin is pulled upward into the interior of the coil.

SUMMARY

It is the object of the present invention to provide a joint mechanism which is also suited for active persons walking with a prosthesis, but is additionally able to be locked by the user even in the extended state in order to ensure full carrying ability in certain situations and, in particular, to enable secure walking and standing in wet areas.

Said object is achieved as claimed in the invention by a mechanism with the features of the main claim. Advantageous developments and further developments of the invention are given in the sub-claims, the description and in the figures.

The joint mechanism as claimed in the invention of a knee orthosis or knee prosthesis having a first part and a second part which is pivotable in relation thereto and connection means for fastening the joint mechanism on a user of the knee orthosis or knee prosthesis, as well as having a locking mechanism, by way of which a pivoting of the two parts relative to one another in the direction of flexion is prevented by means of a positive locking element, which is arranged so as to be displaceable on the second part and, in the locking state, engages in a positive locking manner in a recess associated with the first part, provides that the positive locking element is mounted so as to be rotatable on the second part and has a contour which, in the locking position, projects into the recess and in the release position enables the first part to pivot past the bearing of the positive locking element. The locking mechanism with the positive locking element and the recess brings about a blocking of the knee joint in the direction of flexion by means of blocking the relative movement between the first part and the second part, usually the lower part and the upper part. In principle, the site of the arrangement of the positive locking element and of the recess is freely selectable, as a rule, on account of the simpler assignment and operability, the positive locking element is arranged on the lower part of the joint mechanism, that is on the knee frame, whilst the recess is arranged on the upper part or on a knee head. In the blocked state of the joint mechanism, that is in the locking position of the positive locking element, the movement between the knee head and the knee frame is prevented by means of the rotatably mounted positive locking element. If the knee joint is once again to be able to be bent freely in the direction of flexion, it has to be unlocked by means of a rotation of the positive locking element. As a result, the contour, which is not realized in a rotationally symmetrical manner, is moved into a position in which there is no positive-locking engagement of the positive locking element in the recess which pivots past the positive locking element.

The positive locking element can be prestressed in a spring-loaded manner in the direction of the locking position. As a result, it is possible for the positive locking element to latch into the recess automatically when the first part and the second part of the joint mechanism are oriented with respect to one another such that the locking position is achieved. If the positive locking element is situated in the release position when the two parts of the joint mechanism are not situated in the locking position, a flexion movement and an extension movement are easily possible. If the user of the joint mechanism controls the locking mechanism for example in the bent state of the knee and if this then results in an extension of the joint in the direction of extension, the positive locking element automatically latches into the recess on account of the spring tension and locks the second part against a relative movement with respect to the first part.

The positive locking element can be realized as a bolt with a round or oval cross section with a flattening to form a passages for the first part. The flattening on the bolt can be realized by grinding, milling or by the provision of a recess which is straight, rounded or specially adapted to the bolt. The flattening of the bolt then enables the free movement of the first part in relation to the second part by the first part pivoting past the bolt in the region of the flattening. When the bolt has an oval cross sectional form, in the release position the second part pivots past the contour by way of the short axes, in the locking position the contour engages in the recess by way of the long axis.

It can also be provided that the positive locking element is mounted in an eccentric manner and is pivoted out of the recess by means of a rotation about the pivot axis in order to assume a release position, or is pivoted back in again in order to assume a locking position.

The joint mechanism is preferably realized as a monocentric joint mechanism, the joint mechanism is also preferably water-resistant and, where applicable, is sealed in a watertight manner in relation to the surrounding area. The monocentric development of the joint mechanism means that it is relatively simply constructed such that a ruggedness of the knee joint is provided, by way of which it is possible for the user to carry out a plurality of activities. Monocentric joint mechanisms, for example with a hydraulic or pneumatic damping device which is used to control the swing phase, are also suited for active walkers and on account of the rugged and simple method of construction are also suited for high loads. Consequently, it is possible that increased independence and over and above this increased reliability is ensured in spite of the simple embodiment of the joint providing approximately identical functions when compared with joints with electronic control.

In order to suppress unwanted locking or unlocking of the joint mechanism, the positive locking element is mounted on the second part so as to be secured against rotation such that a securement has first to be overcome in order to perform unlocking or locking.

A spring-loaded fixing device can realize a positive-locking securement of the positive locking element. Alternative fixing devices are possible and provided, for example a fixing device being supplied with power in an electromagnetic or motor-driven manner. It is not possible to move the positive locking element out of the locking position into the release position and vice versa until the fixing device is consciously removed out of the fixed position. The fixing device just as the positive locking element can have associated therewith a device for providing haptic feedback, for example a cam path along which the positive locking element has to be moved so that latching or kinetic resistance has to be overcome. The latching into the respective end position then produces a mechanical pulse which is recognized by the user as haptic feedback such that the positive locking element or fixing device is situated in the one or other position.

A damper, in particular a hydraulic damper, which along with swing phase control as a result of kinetic resistances also provides bending-end-position damping and extension-stop damping, is preferably arranged between the first part and the second part of the joint mechanism. The swing phase control is produced during the swing phase of walking by a correspondingly realized damping characteristic. Said characteristic, in this case, is developed such that a harmonic gait pattern is obtained for the respective user. Part of the harmonic gait pattern is extension-stop damping as well as bending-end-position damping which can be achieved by means of developing flow channels inside the damper. If the damper is realized as a hydraulic damper, the draining away of the hydraulic oil displaced by the piston stroke is effected, for example, through a bore in the piston rod. A narrow, e.g. spiral channel, which is admitted into the surface of the piston rod, opens out into said bore. As soon as the piston closes the bore and the oil has to flow out by means of the channel, there is a gradual rise in the damping brought about by the throttling action and a specially realized channel geometry. The greater the reduction in the cross sectional flow, the greater the rise in damping. Different channel geometries can be realized for the flexion side and the extension side in order to achieve different damping in the direction of flexion and in the direction of extension.

Rotational stops can be associated with the positive locking element such that, for example, with an oval development of the positive locking element rotatability can only be effected about a maximum established angle of rotation, for example 90° or 180°. Depending on the development of the flattening or recess in the positive locking element, which is developed, for example, as a bolt, it is also possible to provide a rotational region limitation for the positive locking element in the case of an otherwise round cross section of the positive locking element.

The fixing device, in order to secure the positive locking elements against unintended actuation, can have associated therewith a remotely-controllable actuator which both eliminates the fixing and moves the positive locking element out of the locking position into the release position and, where applicable, moves it back into the locking position.

BRIEF DESCRIPTION OF THE DRAWINGS

Exemplary embodiments of the invention are explained below by way of the accompanying figures, in which, in detail:

FIG. 6 shows two representations of a variant of the prosthesis knee joint; and FIG. 7 shows two representations of a detail in FIG. 6.

DETAILED DESCRIPTION

Figure 1:
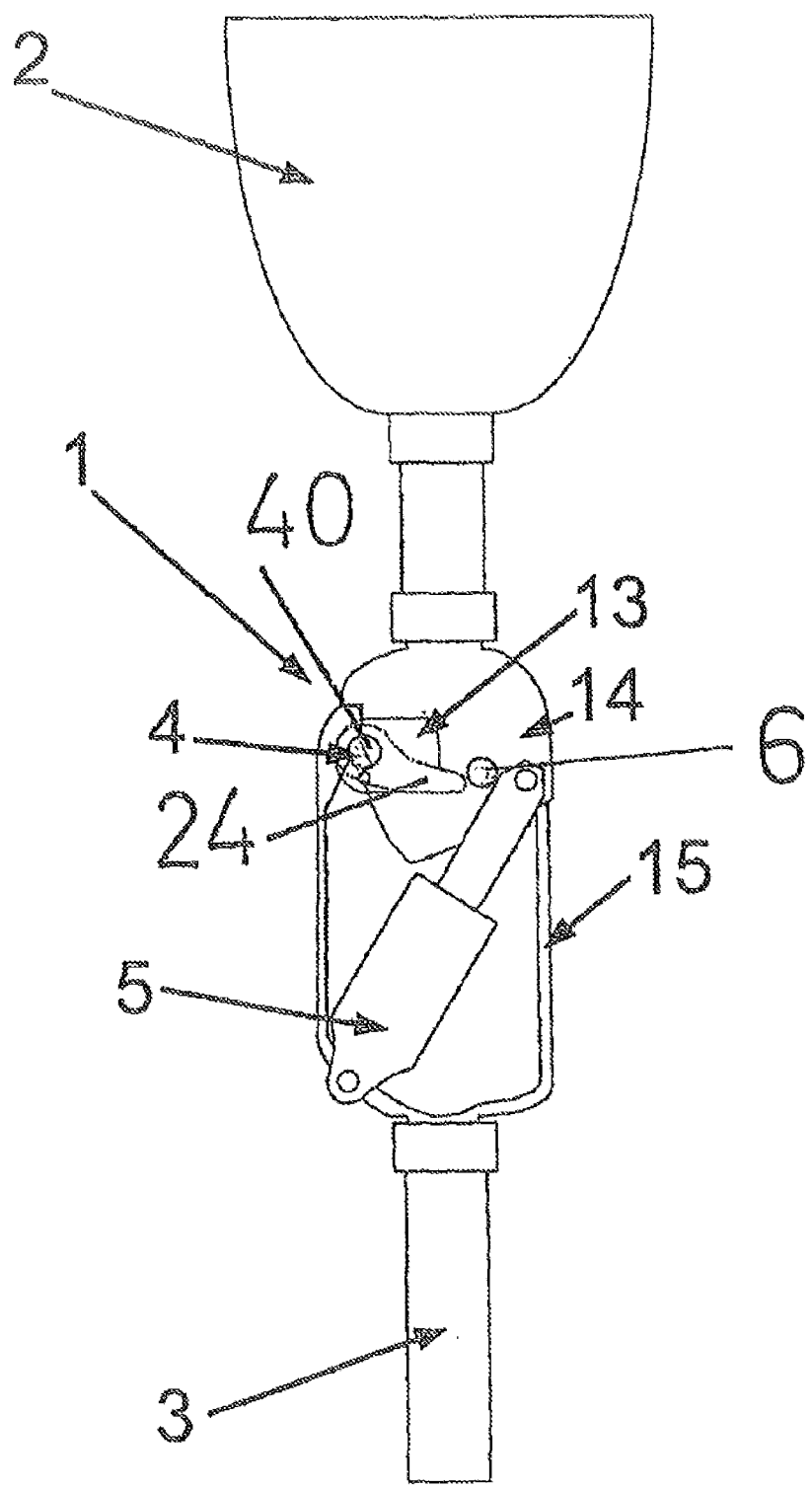
FIG. 1 shows a schematic representation of a side view of a prosthesis knee joint in the locking position.

FIG. 1 shows a schematic representation of a side view of a prosthesis knee joint 1 having an upper leg shaft 2 for securing on a knee joint user as well as a lower leg tube 3. The upper leg shaft 2 serves for receiving an upper leg stump, the lower leg tube 3 serves for receiving a prosthetic foot (not shown). The prosthesis knee joint 1, which has a first part 14 and a second part 15 which is pivotably mounted thereon, is arranged between the upper leg shaft 2 and the lower leg tube 3. The first part 14 is usually designated as the upper part of the prosthesis knee joint 1, the second part 15 usually as the lower part. The prosthesis knee joint 1 is developed in the embodiment shown as a monocentric knee joint, the second part 15, which can also be designated as a knee joint frame, pivots about a pivot axis 6 in relation to the first part 14, which is also designated as a knee joint head. A hydraulic damper device 5 in the form of a hydraulic damper is arranged on the first part 14 on the dorsal side with respect to the pivot axis 6, the bearing point on the second part 15 is on the ventral side with respect to the pivot axis 6. Over and above this, a positive locking element 4, which is realized as a rotatable bolt, is arranged on the second part 15. FIG. 1 shows the prosthesis knee joint 1 in a locking position, the rotatable bolt 4 engages in a recess 40 which is realized on the first part 14. The recess 40 is situated on an outer contour of the first part 14 which pivots past the positive locking element 4 when the prosthesis knee joint 1 is bent. In the locked state shown, the positive locking element 4 realized as a bolt blocks a bending movement between the first part 14 and the second part 15. In principle, it is also possible to arrange the positive locking element 4 on the first part 14, whilst the recess 40 is realized on the second part 15.

In addition, a fixing device 13, which is arranged on the positive locking element 4, can be seen in FIG. 1. The fixing device 13 serves for reversing the positive locking element 4 as well as for activating or deactivating the mechanical block of the prosthesis knee joint 1. Both the design and the method of operation of the fixing device 13 will be explained in more detail subsequently. By means of a lever 24, the positive locking element 4 can be pivoted out of the locking position shown into a release position and vice versa. The locking, in this case, takes place in the extended position, the positive locking element 4 is pivoted into the recess 40 and brings about a positive-locking blocking action.

Figure 2:
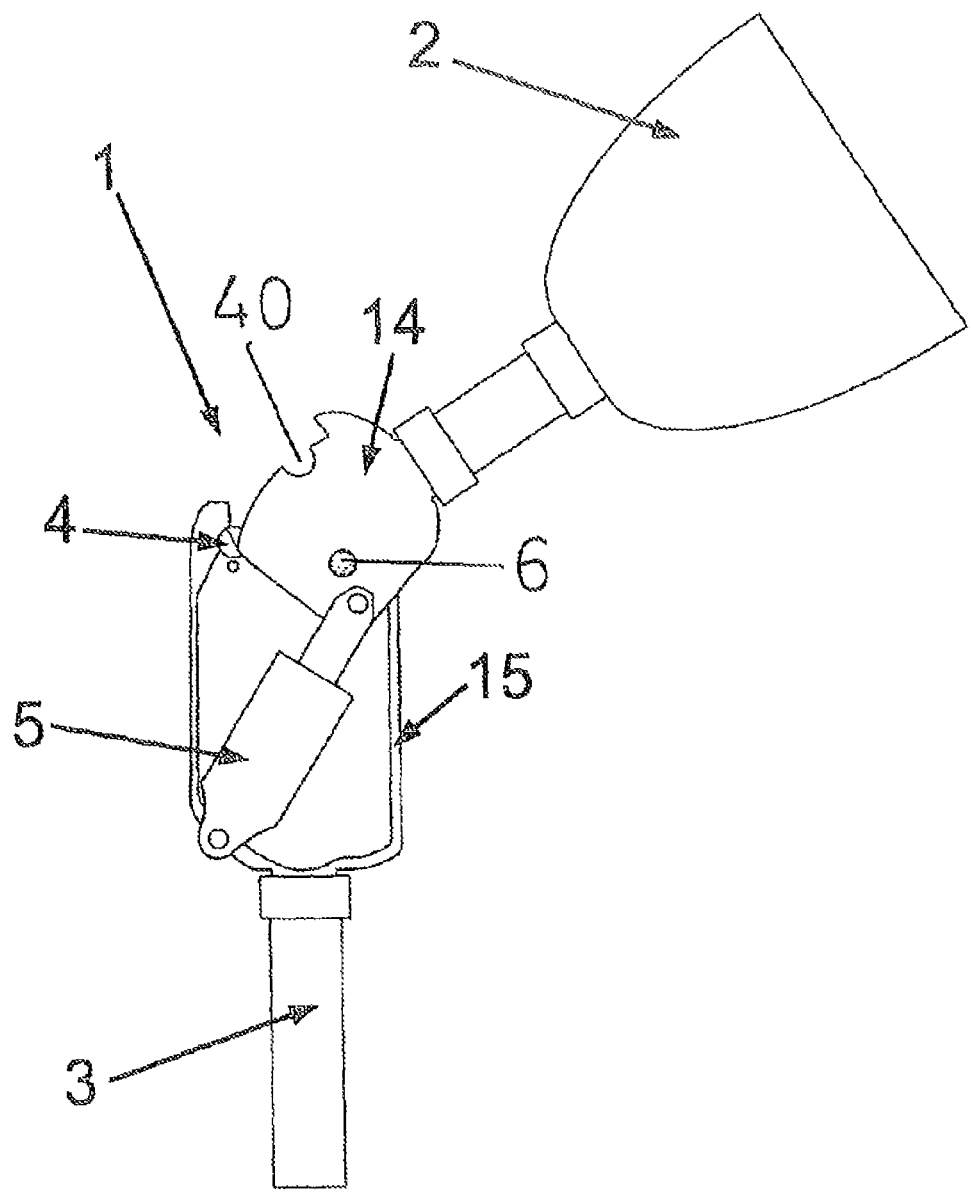
FIG. 2 shows a prosthesis knee joint in the release position.

FIG. 2 shows the prosthesis knee joint 1 in a bent position. The upper leg shaft 2 and the lower leg tube 3 are mounted about the pivot axis 6 in relation to one another, the hydraulic damper 5 is shortened compared to the locking position according to FIG. 1. The recess 40, which has a semi-circular contour in the exemplary embodiment shown, can be seen on the first part 14. Said recess 40 is admitted into the contour of the first part 14 which pivots past the positive locking element 4 when the prosthesis knee joint 1 bends in. The positive locking element 4 has an asymmetrical contour, in the exemplary embodiment shown that region of the positive locking element 4 which is responsible for the locking action is realized as a semicircle. If that half of the semicircle without material lies opposite the recess 40, the positive locking element is situated in a release position, if the solid part of the positive locking element 4 projects right into the recess 40, either totally or at least in part, the prosthesis knee joint 1 is blocked against bending. Through the semicircular form of both the positive locking element 4 and of the recess 40 and of the locking in the extended position, it is not necessary for the positive locking element 4 to latch in the recess completely, rather just a relatively small overlap and a projection of the solid part is sufficient to bring about a blocking action.

As soon as the positive locking element 4 has moved out of the locking position into the release position and the first part 14 has been pivoted about the pivot axis 6 in relation to the second part 15 such that the recess 40 has been displaced so far away from the positive locking element 4 that the solid part of the positive locking element 4 is no longer able to engage in the recess 40, the prosthesis knee joint 1 can always be bent and extended as far as up to the new locking action.

The positive locking element 4, in this case, can be provided with a preliminary tension, in particular a preliminary spring tension, which displaces the positive locking element 4 into a locking position. FIG. 2 shows the position where the first part 14 has been pivoted so far that the positive locking element 4 no longer slides along on the slightly bent outer contour below the recess 40. The positive locking element 4 is situated on the bottom edge of the first part 14 in a position in which it could engage in the recess 40. More extensive bending is easily possible. If, proceeding from the position in FIG. 2, the prosthesis knee joint 1 is extended, the underside of the first part 14 comes into contact with the positive locking element 4 in such a manner that it is pivoted into a release position. In the case of further extension, the positive locking element 4 then slides along on the contour of the first part 14 which faces the positive locking element 4 just so far until the recess 40 is reached. On account of the spring tension, the positive locking element 4 then automatically pivots into the locking position and locks the prosthesis knee joint 1 in the extended position, as is shown in FIG. 1.

Figure 3:
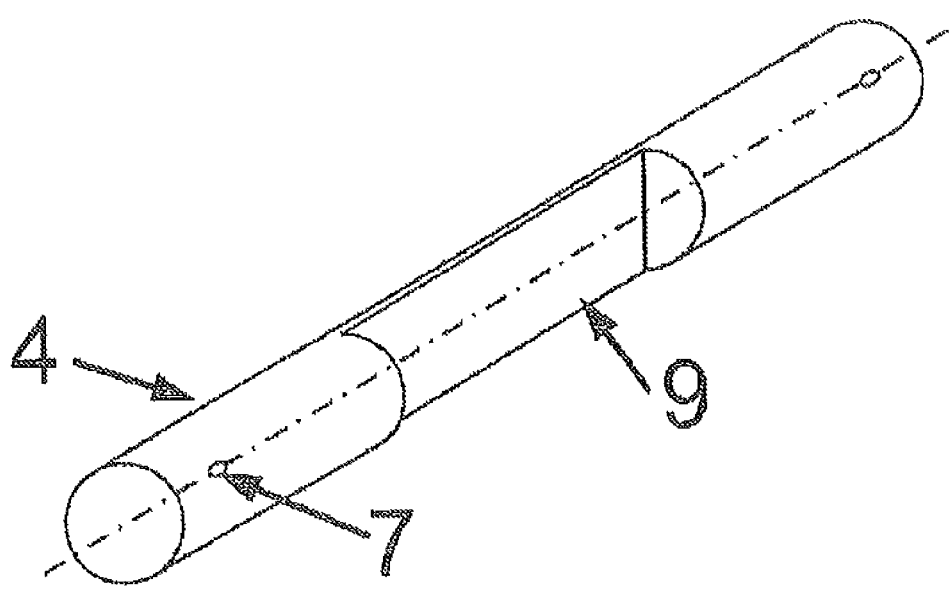
FIG. 3 shows a positive locking element as a bolt.

FIG. 3 shows a representation of a detail of the positive locking element 4. The positive locking element 4 is realized as a cylindrical bolt with a centrally arranged flattening 9. The flattening 9 serves for the release of a relative movement between the first part 14 and the second part 15. The flattening 9 provides space for the first part to pivot past or pivot through the flattening 9 such that the prosthesis knee joint 1 is able to be bent. A recess 7 for receiving a fixing pin is realized on at least one end region of the positive locking element 4. The positive locking element 4 is protected against unintended rotation by means of the fixing pin, which will be explained in more detail in FIG. 5.

Figure 4:
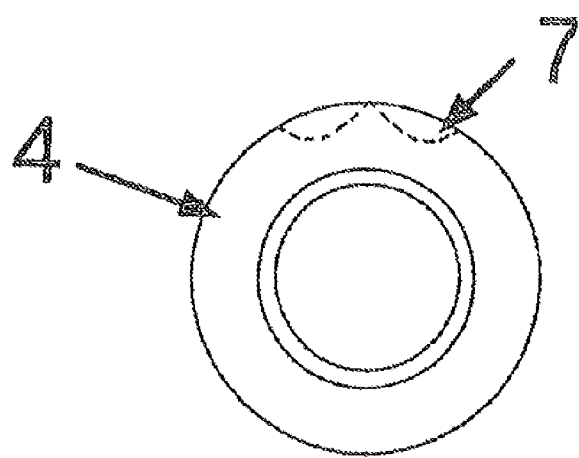
FIG. 4 shows a sectional representation of the positive locking element.

FIG. 4 shows a sectional representation in which two recesses 7 are indicated for the fixing pin, the one recess 7 fixes the positive locking element 4 in the locking position, the other in the release position.

Figure 5:
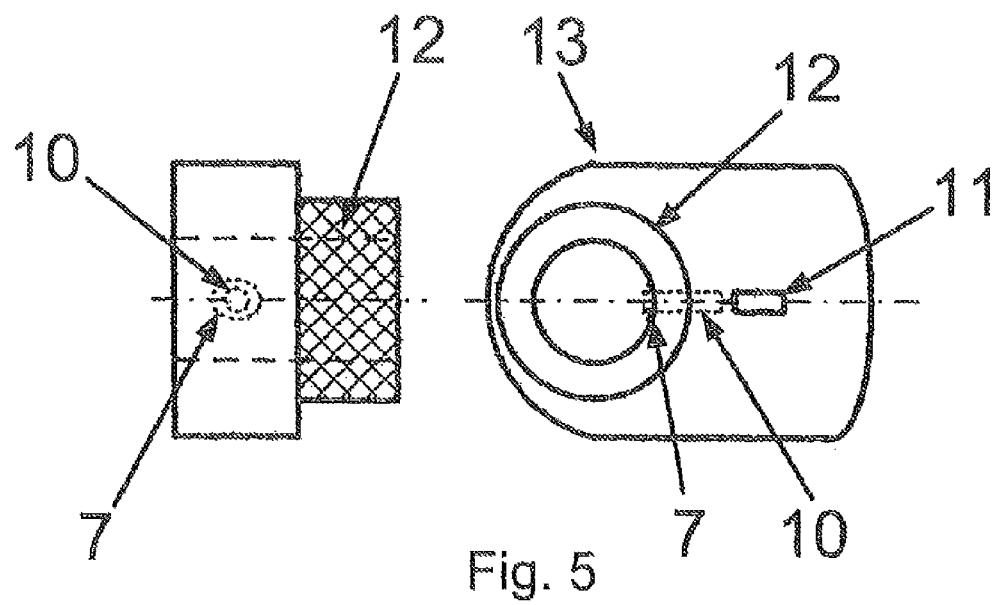
FIG. 5 shows a representation of a detail of a fixing device.

FIG. 5 shows two views of the fixing device 13. A device 12 for reversing or for activating or deactivating a mechanical blocking means is arranged on the fixing device 13. The device 12 switches between the states "blocked" and "not blocked". In this case, an actuator 11 is provided in the device 12, by means of which actuator a fixing pin 10 can be moved into the recess 7 or can be moved out of the recess 7. The actuator 11 serves for acting on the fixing pin 10 by way of a constrained force which either moves the fixing pin 10 out of the recess 7 or presses it into the recess 7 inside the positive locking element 4.

The locking and unlocking mechanism shown with the positive locking element 4 is similar to a linear cam, as is used in a mechanical gear unit. In this case, the positive locking element 4 can be triggered, for example, by means of the lever 24, as is shown in FIG. 1, either manually or in a remotely-controlled manner by means of an actuator. Other actuating elements can also be provided, for example an adjustable screw or a motor. In the exemplary embodiment shown, the lever 24 is pivoted downward about the pivot axis of the positive locking element 4 such that the first part 14 of the prosthesis knee joint 1 is able to pivot right through the flattening 9. In the blocked state, the movement between the first part 14 and the second part 15 is prevented by the solid part of the halved bolt. The blocking of the prosthesis knee joint 1 can only be effected in the extended knee position, as only in said position can a relative movement between the first part 14 and the second part 15 be prevented by means of a positive-locking engagement of the solid part of the positive locking element 4 in the recess 40.

The positive locking element 4 can be secured in the desired position by the fixing device 13, preferably by means of the fixing pin 10, which is pressed into a corresponding recess 7 inside the positive locking element 4 by means of spring force, a cable pull or in a motor-driven manner and, as a result, prevents a rotation of the positive locking element 4 in relation to the second part 15, that is to its bearing position. The overcoming of the spring force, that is the unblocking of the positive locking element 4 is effected in a preferred manner manually or also by means of remote control such that the positive locking element 4 is then able to be reversed between the open and the blocked position.

If the prosthesis wearer operates the locking mechanism when the knee is bent, the positive locking element 4 is moved into the locking position, the prosthesis knee joint 1, however, continues to remain freely movable in the direction of flexion. When the prosthesis knee joint is extended, the positive locking element 4 is once again rotated into the release position in which the joint is unblocked. Insofar as the positive locking element 4 is not acted upon in a permanent manner in the direction of a locking position, then the prosthesis knee joint 1 remains unblocked. If a preliminary tension or preliminary load is provided in the direction of the locking position, the positive locking element latches into the recess 40 automatically when reaching an extended position and locks the prosthesis knee joint 1.

When the fixing device 13 is actuated by the positive locking element 4, just as in the case of the blocking mechanism, it is advantageous when the prosthesis user receives haptic feedback in order to make the prosthesis user aware in multiple ways that changeover has occurred between an unlocked and a locked state.

In place of half a bolt, the positive locking element can also be realized as a pivotable strip with a corresponding actuating lever 24 and spring preloading. The recess 40 is then preferably no longer realized as a semicircle but as a recess which corresponds to the cross section of the strip.

The prosthesis knee joint 1 is a so-called monocentric modular light knee joint with an integrated miniature hydraulic system 5. The hydraulic system 5 is used to control the swing phase and in so doing generates dynamic kinetic resistances which optimize the gait pattern by preventing too wide a swing through in bending or too hard a stop in extension. The blocking of the prosthesis knee joint is controllable by way of the positive locking element 4 by means of the lever 24 or another actuator. The lever 24, the positive locking element 4 or the actuator can be fixed in the respective end positions, both in the locking position and in the release position, by means of a knurled screw, an adjusting screw or an axially displaceable bolt. The two positions with the respective recesses 7 are shown in FIG. 4. As a result, it is possible to fix the positive locking element 4 both in the locking position and in the release position.

FIG. 6 shows two representations of a prosthesis knee joint 1 in the closed and the open position. In the left-hand representation, the first part 14 or the upper part is shown in a locking position. The upper part 14 is mounted so as to articulate about the pivot axis 6, the pivoting movement can be influenced by the damping device 5. The positive locking element 4 is mounted on the lower part 15 so as to be pivotable about a pivot axis 44. Differently to the embodiment according to FIGS. 1 and 2, the positive locking element 4 is mounted about a pivot axis 44 which is arranged eccentrically with respect to the positive locking element 4. The positive locking element 4, consequently, can also have a full circular cross section in the region of the engagement into the recess 40 as when the positive locking element 4 is rotated out of the locking position into the release position, the positive locking element can pivot out of the recess 40 and can remain outside the pivot path which is covered by the upper part 14 during pivoting.

In order to allow the positive locking element 4 to pivot out of the recess 40, a recess 41 is provided on the lower part 15, into which recess the positive locking element 4 is able to pivot.

In the right-hand representation, the prosthesis knee joint 1 is shown in a release position where the positive locking element 4 is pivoted out of the recess 40 in the upper part 14 and pivoted into the recess 41 in the lower part 14. In the release position, the upper part 14 can be pivoted past the positive locking element 4 without any blocking taking place.

By selecting the position of the pivot axis 44 in a suitable manner, it is possible to create different preferred positions. Thus, for example, it is possible for the position of the pivot axis 44 to be selected without preliminary spring tension such that initially a release position is always assumed, as is shown in the right-hand representation in FIG. 6; as an alternative to this, an alignment in the direction of the recess 40 of the upper part 14 can be effected such that the prosthesis knee joint 1 is basically locked without a separate unlocking movement.

The positive locking element 4 is effectively prevented from being pulled out of the locking position when the upper part 14 is moved in the direction of flexion about the pivot axis 6 by the circular form of both the positive locking element 4 and of the recess 40 and the recess 41. FIG. 7 shows representations of detail of the different positions of the positive locking element. In the top representation, the prosthesis knee joint is situated in a locking position, the positive locking element 4 is pivoted around its pivot axis 44 in the direction of the upper part 14 such that it is not possible for the upper part 14 to pivot. In the bottom representation, the positive locking element 4 is pivoted out of the recess 40 about the pivot axis 14 mounted on the bottom part 15 such that the upper part 14 is able to pivot past the bottom part 15 such that the prosthesis knee joint 1 is able to be bent. An elliptical or an angular contour of the positive locking element 4 can also be provided as an alternative to a circular cross sectional development.

The invention claimed is:

1. A joint mechanism of a knee orthosis or knee prosthesis, comprising:
    a first part and a second part, which is pivotable in relation thereto, and
    a connector for fastening the joint mechanism on a user of the knee orthosis or knee prosthesis,
    a locking mechanism, by way of which a pivoting of the two parts relative to one another in the direction of flexion is prevented with a positive locking element, which is arranged so as to be displaceable on the second part and, in a locking position, engages in a positive locking manner in a recess associated with the first part, the positive locking element being mounted so as to be rotatable on the second part and has a contour which, in the locking position, projects into the recess and in a release position enables the first part to pivot past the positive locking element,
    wherein the positive locking element comprises a bolt with a round or oval cross section with a flattening, which forms a passage for the first part.

2. The joint mechanism as claimed in claim 1, wherein the positive locking element is prestressed in a spring-loaded manner in a direction of the locking position.

3. The joint mechanism as claimed in claim 1, wherein the positive locking element is mounted in an eccentric manner on the second part.

4. The joint mechanism as claimed in claim 1, wherein the joint mechanism comprises a monocentric joint mechanism.

5. The joint mechanism as claimed in claim 1, wherein the positive locking element is mounted on the second part so as to be secured against rotation.

6. The joint mechanism as claimed in claim 1, wherein a spring-loaded fixing device provides a positive-locking securement of the positive locking element.

7. The joint mechanism as claimed in claim 1, wherein the positive locking element is displaceable along its axis of rotation.

8. The joint mechanism as claimed in claim 1, wherein a damper is arranged between the first part and the second part.

9. The joint mechanism as claimed in claim 1, wherein the recess is arranged on the first part such that the locking position is present in an extended position of the joint mechanism.

10. The joint mechanism as claimed in claim 1, wherein the positive locking element includes rotational stops.

11. The joint mechanism as claimed in claim 6, wherein the fixing device includes a remotely-controllable actuator.

12. A joint mechanism of a knee orthosis or knee prosthesis, comprising:
- a first part;
- a second part being pivotable relative to the first part;
- a connector configured to fasten the joint mechanism on a user of the knee orthosis or knee prosthesis;
- a locking mechanism having a positive locking element and a recess, the recess being formed in the first part, and the positive locking element being mounted on the second part and having a locking portion arranged to engage the recess to prevent pivoting of the first and second parts relative to one another in a flexion direction when the positive locking element is in a locked position, and the locking portion permits the first part to pivot relative to the second part when the positive locking element is in a released position;
- wherein the positive locking element includes a bolt with a round or oval cross section, which when engaged in the recess provides the locked position, and a flattened portion which when aligned with the recess provides the released position.

13. The joint mechanism as claimed in claim 12, wherein the positive locking element is biased in the direction of the locking position.

14. The joint mechanism as claimed in claim 12, wherein the positive locking element is axially movable about its longitudinal axis between the locked and released positions.

15. The joint mechanism as claimed in claim 12, wherein the joint mechanism comprises a monocentric joint mechanism.

16. The joint mechanism as claimed in claim 12, wherein the positive locking element is mounted on the second part so as to be secured against rotation.

17. A joint mechanism of a knee orthosis or knee prosthesis, comprising:
- a locking mechanism having a positive locking element and a recess;
- a first part carrying the recess;
- a second part pivotably mounted to the first part and carrying the positive locking element;
- wherein the positive locking element includes a locking portion and is rotationally movable between a locked position in which the locking portion engages the recess to restrict relative pivotal movement between the first and second parts in a flexion direction, and a released position in which the locking portion is removed from the recess to permit relative pivotal movement between the first and second parts in the flexion direction;
- wherein the positive locking element includes a bolt with a round or oval cross section, which when engaged in the recess provides the locked position, and a flattened portion which when aligned with the recess provides the released position.

* * * * *